(12) United States Patent
Bertazzoni et al.

(10) Patent No.: US 9,408,700 B2
(45) Date of Patent: *Aug. 9, 2016

(54) CONTAINER AND SYSTEM OF CONTAINERS OF SURGICAL INSTRUMENTS FOR KNEE SURGERY

(71) Applicants: DEPUY INTERNATIONAL LIMITED, Leeds, West Yorkshire (GB); DEPUY (IRELAND), Cork (IE)

(72) Inventors: Mario Bertazzoni, Montreux (CH); Michael Reeve, Tadcaster (GB); Alberto Verteramo, Turin (IT)

(73) Assignee: DEPUY (IRELAND), Cork (IE)

(*) Notice: Subject to any disclaimer, the term of this patent is extended or adjusted under 35 U.S.C. 154(b) by 87 days.

This patent is subject to a terminal disclaimer.

(21) Appl. No.: 14/253,933

(22) Filed: Apr. 16, 2014

(65) Prior Publication Data

US 2014/0224704 A1    Aug. 14, 2014

Related U.S. Application Data

(63) Continuation of application No. 13/003,411, filed as application No. PCT/GB2009/050808 on Jul. 9, 2009, now Pat. No. 8,701,890.

(30) Foreign Application Priority Data

Jul. 10, 2008  (GB) ................................. 0812555.1

(51) Int. Cl.
*B65D 71/00* (2006.01)
*A61B 17/58* (2006.01)
(Continued)

(52) U.S. Cl.
CPC ................. *A61F 2/38* (2013.01); *A61B 17/154* (2013.01); *A61B 19/02* (2013.01); *A61B 19/0271* (2013.01); *A61B 2019/0278* (2013.01)

(58) Field of Classification Search
CPC ............... A61B 19/02; A61B 19/0271; A61B 2019/0278; A61B 17/154
USPC ................. 206/63.5, 363, 368, 369, 370, 438, 206/570–572; 606/88, 89, 99, 104; 623/16.11, 17.11, 20.14, 20.15, 20.32, 623/20.35
See application file for complete search history.

(56) References Cited

U.S. PATENT DOCUMENTS

| 4,730,726 A | * | 3/1988 | Holzwarth | ......... A61B 19/0271 206/204 |
|---|---|---|---|---|
| 5,318,543 A |  | 6/1994 | Ross |  |

(Continued)

FOREIGN PATENT DOCUMENTS

| DE | 202007000934 U1 | 4/2007 |
|---|---|---|
| EP | 1393695 A1 | 3/2004 |

(Continued)

OTHER PUBLICATIONS

Zimmer, Inc., "Instrument Care, Cleaning and Sterilization Instruction"; www.zimmer.com; Feb. 6, 2004; Retrieved Jan. 6, 2011 from the Internet URL: http://www.zimmer.co.nz/web/enUS/pdf/Surgical_Cleaning_Instructions_Final.pdf ; © 1987, 1988, 2002 Zimmer Inc.; USA , 18 pages.

*Primary Examiner* — Luan K Bui

(57) ABSTRACT

A system of surgical instruments for use with at least a first implant and a second implant of the same type but different sizes is provided. The system includes at least three containers. The first container contains at least a first surgical instrument of a first type that is size specific and a second surgical instrument of a second type that is size specific; both the first and second instruments are of a first size The second container contains at least a third surgical instrument of the first type and a fourth surgical instrument of the second type; both the third and fourth instruments are of a second size which is different from the first size. The third container contains at least a fifth surgical instrument of a third type which is size independent.

11 Claims, 4 Drawing Sheets

(51) Int. Cl.
*A61F 2/38* (2006.01)
*A61B 17/15* (2006.01)
*A61B 19/02* (2006.01)

(56) References Cited

U.S. PATENT DOCUMENTS

| | | | |
|---|---|---|---|
| 5,597,384 A | 1/1997 | Walker | |
| 5,776,201 A | 7/1998 | Colleran | |
| 5,779,053 A | 7/1998 | Partika | |
| 6,158,437 A | 12/2000 | Vagley | |
| 6,783,004 B1 | 8/2004 | Rinner | |
| 6,793,078 B2 | 9/2004 | Roshdy | |
| 8,079,468 B2 * | 12/2011 | Pleil | A61B 19/40 206/339 |
| 8,584,853 B2 * | 11/2013 | Knight | A61B 19/46 206/339 |
| 2003/0121821 A1 | 7/2003 | Roshdy | |
| 2005/0033430 A1 | 2/2005 | Powers | |
| 2006/0217815 A1 | 9/2006 | Gibbs | |
| 2006/0223035 A1 | 10/2006 | Fischer | |
| 2007/0034538 A1 | 2/2007 | Landis | |
| 2009/0194446 A1 | 8/2009 | Miller | |

FOREIGN PATENT DOCUMENTS

| | | |
|---|---|---|
| FR | 2904527 A1 | 2/2008 |
| WO | WO 0152762 A1 | 7/2001 |
| WO | WO 2004006811 A2 | 1/2004 |
| WO | WO 2005016183 A1 | 2/2005 |

\* cited by examiner

CONTAINER AND SYSTEM OF CONTAINERS OF SURGICAL INSTRUMENTS FOR KNEE SURGERY

This Application is a CON of Ser. No. 13/003,411, filed on Feb. 2, 2011, U.S. Pat. No. 8,701,890. The present invention relates to a container and a system of containers of surgical instruments, and in particular orthopaedic surgical instruments for knee surgery.

Any surgical procedure typically requires a number of instruments. In order to simplify inventory and procedure in the operating room it is known to group the instruments required in a surgical procedure together in one or more trays.

US-2006/0223035 (Fischer) discusses a collection of dental sub-kits for use in placing a dental post in a prepared recess. The surgical procedure for placing a dental post is relatively simple. As such, Fischer proposes to provide a number of sub-kits in which instruments are grouped by size, so that each sub-kit has instrumentation corresponding to a particular size. A dental practitioner selects a sub-kit of a desired size and then uses the relevant components to prepare the recess and insert the post. All the instruments required by a dental practitioner for the procedure are provided in a single container or sub-kit and the remaining sub-kits are not used.

While the sub-kit of Fischer can be useful in relatively simple surgical procedures, it does not scale easily to complicated surgical procedures, for example orthopaedic surgery such as knee surgery. Knee surgery is more complicated, involving more surgical steps and potentially more instruments (over 100 items taken into the operating theatre). Furthermore, individual surgeons may adapt the surgical procedure depending on the circumstances of the patient and the philosophy of the surgeon. For example, the surgeon may choose to adopt a fixed bearing or a mobile bearing or to use a cruciate retaining or a cruciate sacrificing methodology. As a result, instrumentation for knee surgery has been grouped for flexibility in the surgical method.

Orthopaedic surgery typically requires a large number of instruments during the surgical procedure. It is known to provide these tools in a number of trays, with each tray containing several instruments. The trays can then be sterilised with the tools in place and sealed before they are required during surgery. Once the seal on the tray has been broken it is necessary to sterilise all the instruments and reseal the tray before they can be used in another surgical procedure, even if some of the instruments have not been used.

For example, the P. F. C Sigma Total Knee System, which is commercially available from DePuy International Limited, typically requires surgical instrumentation in six trays, four of which have two levels. The number of instruments supplied depends on the surgeon preference and philosophy. In one configuration, a total of 134 instruments are provided. In other knee surgery systems as many as 162 instruments may be provided. The instruments in the trays include those where typically only a single one of each instrument type is required, such as instrument handles, resection tools and measuring devices. In addition, the instruments in the trays include size specific instruments such as trial implants for evaluating the success of the resections for the implant and the performance of the implant before implanting the final implant. Other size specific instruments include cutting guides or broaches for preparing the bone prior to trial and implantation. In the Sigma Total Knee System there are several types of implant, and therefore trial implant, and each type has a variety sizes. For example, one set of size specific instruments relates to the femoral implant and includes femoral notch guides and left and right femoral trials in five different sizes.

In a conventional tray system, such as is currently used in the P. F. C Sigma Total Knee System, the instruments are grouped together in trays that correspond to the surgical method, so that once a tray has been opened, in general the instruments required by the surgeon at a particular stage in the surgery are available for use. This simplifies the operating room procedure and enables the large number of instruments used in orthopaedic surgery to be kept track of more easily.

In such a system the trial implants are grouped together by type in a tray, so that the surgeon has access to all trials of the same type once a tray has been opened. For example, in the P. F. C. Sigma Total Knee System, a single tray contains instruments associated with cutting the femur, including cutting blocks in five different sizes. A second tray contains various types of femoral trial implants, again in five different sizes.

By grouping the instrumentation together in trays, the theatre staff and surgeon can keep track of the large number of instruments more easily. However, this system presents a disadvantage because during a typical procedure usually around 26 instruments (approximately 20%) are be used. The trays will all have been opened and all the instruments require sterilisation before they can be reused, or will require disposal in the case of disposable instruments. As result significant additional costs are incurred in decontaminating (cleaning and sterilising) or disposing of instruments which were not used in the operating room, but which were contained in open trays.

It would be desirable to reduce the number of instruments which were not used in complicated surgical procedures but which still require decontamination or disposal. Sterilising and packaging each instrument separately is impractical because of the need to maintain organisation, minimise packaging cost and waste and avoid use of excessive space in the operating room.

Accordingly, the present invention provides a system of containers holding surgical instruments of different types but of only a single size, which is the same across all the instruments in the container.

The applicant has identified that the biggest potential to save on opening redundant instrumentation is with size specific instruments. A surgeon may have some idea of the size of implant required for a particular patient from x-ray templating. As such, the surgeon will typically be able to identify close to the ideal implant size and choose appropriately sized instrumentation. By providing a container holding different types of instrumentation, but of only one size common to all the instruments in the container, the number of instruments which have not been used and yet are still required to be decontaminated or disposed of is reduced. In the prior art systems for knee surgery, even if the surgeon could identify the correct size and hence use instrumentation of only one size, all the instrumentation of other sizes would require sterilisation despite not having been used. The system proposed by Fischer to use a single sub-kit with all instrumentation cannot be scaled to complex procedures such as knee surgery because of the number of instruments and variables involved; it is not feasible to provide all the instruments for knee surgery in a single sub-kit of a particular size.

According to the present invention there is provided a system comprising at least:
  a first container containing at least a first surgical instrument of a first type that is size specific and a second surgical instrument of a second type that is size specific, wherein both the first and second instruments are of a first size; and
  a second container containing at least a third surgical instrument of the first type and a fourth surgical instrument of the second type, wherein both the third and fourth instruments are of a second size which is different from the first size;

a third container containing at least a fifth surgical instrument of a type which is size independent.

The reference to a "type" of surgical instrument refers to type of surgical instruments that perform the same function. The reference to a "size specific" type of surgical instrument refers to the surgical instruments that are provided in a variety of different sizes. The reference to a "size" of surgical instrument refers to the range of different implant sizes available to the surgeon. For example, a left femoral trial implant is a type of surgical instrument that is size specific and it may be available in sizes, 2, 2.5, 3, 4 and 5. The number used to refer to the size of the trial in this example refers to the sizing system used in the P.F.C. Sigma knee system, it will be appreciated that any size may be used depending on the particular surgical instruments and procedure.

A system according to the invention saves on the number of instruments opened but not used in a complex surgical procedure while still obtaining the benefits of functional grouping. The first and second container, with size specific instruments, can be grouped according to the function of the instruments. This saves on opening instruments of a size that will not be used. The third container contains instruments which are size independent, i.e. the same instrument is used independent of the size of the implant. Thus, the third container may contain instruments that are used in different stages in the procedure, or in more than one stage of the procedure. The third container avoids the need to provide the same common instrumentation in every size-specific container. It also allows the number of containers overall to be reduced because a separate container for each stage in the procedure need not be provided. Contrary to the teaching of Fischer (which suggests grouping all the instruments for the procedure into a single container by size) or prior art knee surgery systems (which groups purely by stages in the surgical procedure), the present invention allows a hybrid organisation where size specific instruments can be grouped in containers by stage in the surgical procedure and by size, and size independent instruments can be provided in a separately, not necessarily limited by their use in a particular stage of the surgical procedure.

It has been found that in a system with containers according to the present invention the instrument usage efficiency (the number of instruments opened and used in a procedure) is generally at least 71% (twenty four instruments opened in the operating room and at least seventeen used). In contrast the instrument usage efficiency for a conventional prior art knee surgery container system may be as low as 16% (one hundred and sixty two instruments opened in the operating room and only twenty five used). This provides a reduction in the number of instruments that must be sterilised or disposed after a procedure. An additional advantage is that the space required in the operating room is reduced.

In an advantageous embodiment, the fifth surgical instrument may be for determining the required size of the first surgical instrument and/or the second surgical instrument. For example, the fifth surgical instrument may be a measurement instrument or sizing guide. This allows the correct size to be determined so that only the first or second container with instruments of the determined size need be opened. In this embodiment the third container is opened before the first and second containers.

The containers may be double bagged or double packaged. With this feature the sterilised container containing the sterilised instruments is sealed in a first bag and then a second bag is sealed around the first bag. This enables the sterilised container to be stored in non-sterile conditions. In an embodiment which is also disposable once packed (double bagged) the whole pack is sterilised such that the inner layers and instruments retain sterility. In an alternative embodiment the container may be single sealed with a filter.

The containers and/or instruments therein may be disposable or reusable.

The containers may comprise a housing defining locations for the at least first and second surgical instruments. In one embodiment the housing may be a tray with recesses sized to receive the at least first and second instruments, When the system is for use in knee surgery, the first and third instruments may be a trial femoral implant and the second and fourth instruments may be for performing femoral finishing resections suitable for the first or third trial femoral implant, respectively. In a particular embodiment, the containers may contain a notch guide, a femoral finishing cutting block, a left trial femoral implant and a right trail femoral implant.

In another embodiment when the system is for use in knee surgery, the first surgical instrument may be a tibial trial instrument of a first thickness and a first size, the second surgical instrument may be a tibial trial instrument of a second thickness and the first size, the third surgical instrument may be a tibial trial instrument of the first thickness and a second size, and the fourth surgical instrument may be a tibial trial instrument of the second thickness and the second size. In this embodiment, the different thickness of tibial trial insert are different types of the instrument because each thickness can be provided in a number of sizes.

In one embodiment, for use in knee surgery, the first and second container may contain instruments for femoral finishing and trial and the third container may contain at least one of primary cuts instrumentation, core instrumentation, patella instrumentation and resection gap trialling/ligament tensing instrumentation. This embodiment may further comprise fourth and fifth containers containing instruments for tibial preparation and tibial trial.

The present invention may use a container containing at least first and second surgical instruments as part of a system of containers, wherein:

the first surgical instrument is of a first type that is size specific;

the second surgical instrument is of a second type that is size specific;

both the first and second surgical instruments are of the same size; and the container contains no other surgical instruments of the first type and the second type.

Embodiments of the invention will now be described by way example with reference to the accompanying drawings in which.

Figure 1:
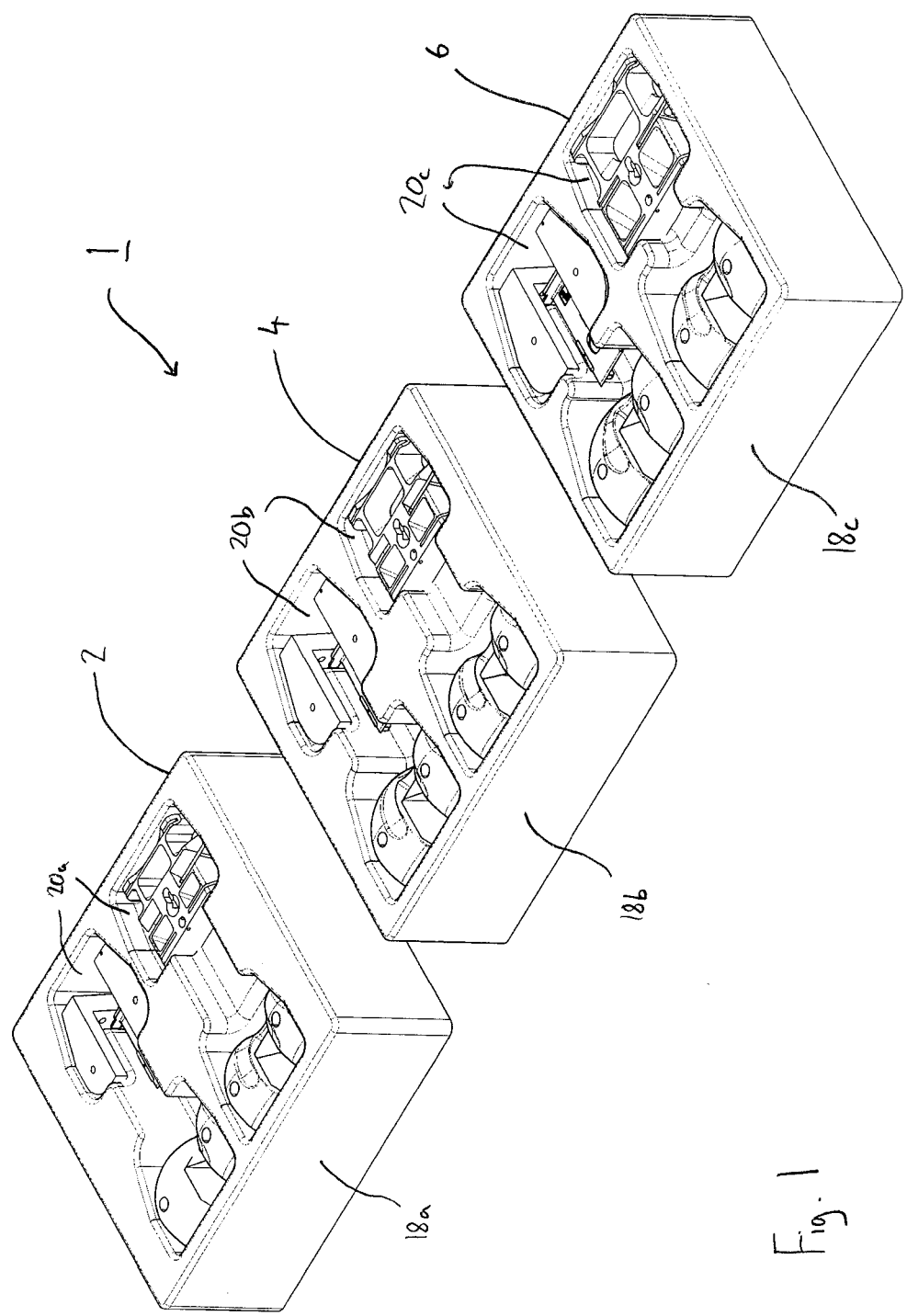
FIG. 1 depicts a perspective view of a system of containers according to a first embodiment of the present invention.
Figure 2:
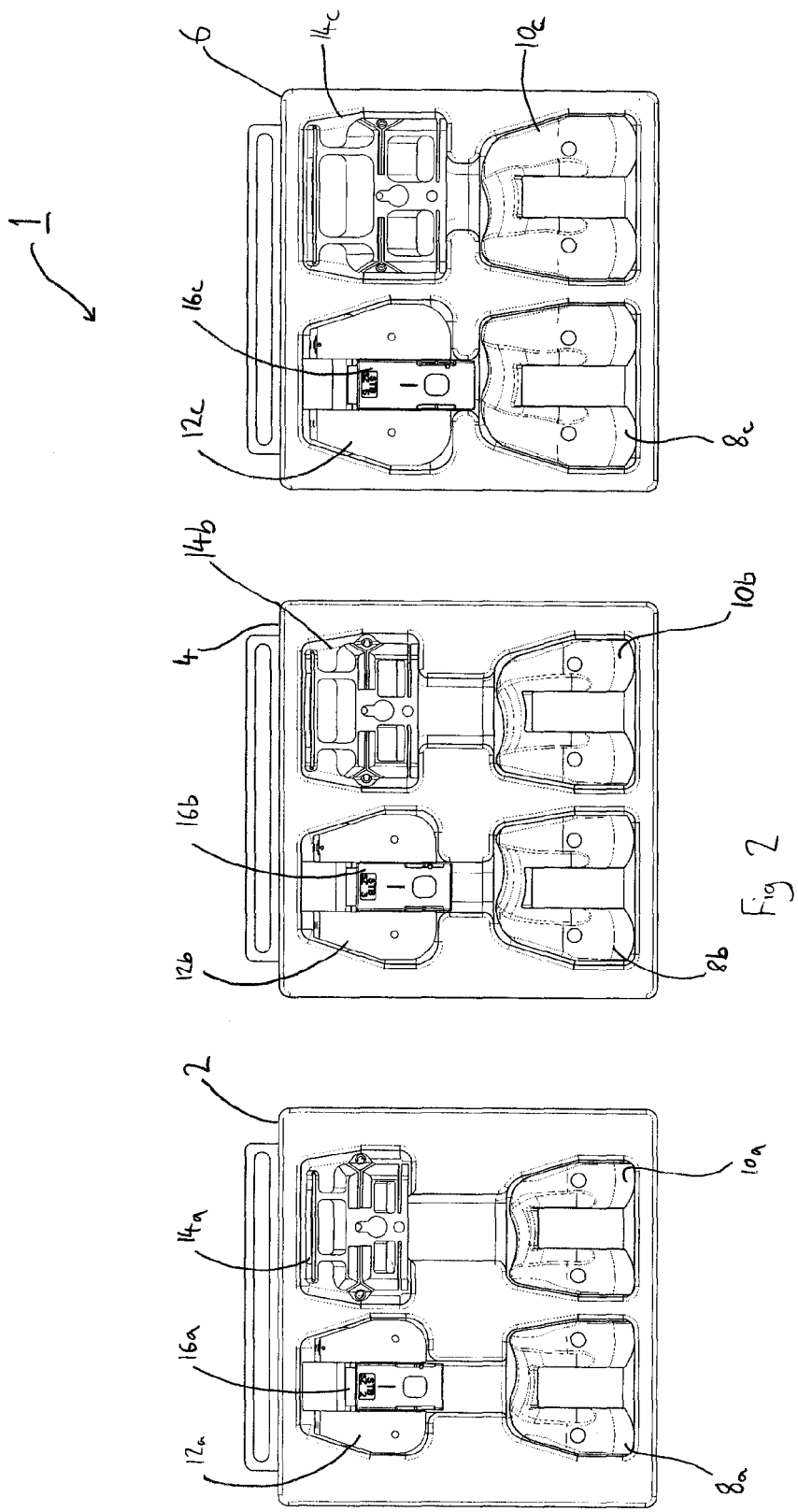
FIG. 2 depicts a plan view of the systems of containers in FIG. 1.

FIG. 1 depicts a perspective view of a system of containers 1 according to an embodiment of the present invention. FIG. 2 depicts a plan view of the system of containers 1 so that their contents can be seen more clearly. Each of the containers 2, 4, 6 in the system 1 contains the same type of instruments as the others of the containers 2, 4, 6 in the system 1. However, each container 2, 4, 6 contains instruments of a single size, which is different from the other of the containers 2, 4, 6. The instruments relate to femoral finishing and trial in a knee replacement procedure.

As can be seen most clearly in the plan view in FIG. 2, each of the containers 2, 4, 6 contains a left femoral trial 8*a*, 8*b*, 8*c*, a right femoral trial 10*a*, 10*b*, 10*c*, a femoral notch guide 12*a*, 12*b*, 12*c*, a femoral cutting block 14*a*, 14*b*, 14*c* and a posterior stabilised box trial 16*a*, 16*b*, 16*c*. Within each container all the instruments have a common size. In this embodiment the instruments are provided for use with the P.F.C. Sigma knee system commercially available from DePuy International Ltd. Container 2 contains instruments of size 2, Container 4 contains instruments of size 3 and container 6 contains instruments of size 4. These sizes relate to the specific sizes defined in the P.F.C. Sigma knee system and if a different system is used, the sizes and their nomenclature may be different.

Each container 2, 4, 6 comprises a housing 18*a*, 18*b*, 18*c* which defines recesses 20*a*, 20*b*, 20*c* for receiving the instruments, as can be seen most clearly in FIG. 1. The recesses 20*a*, 20*b*, 20*c* are appropriately sized to receive instruments of the size contained in the container. In other words, the recesses 20*a* are smaller than the recesses 20*b* and the recesses 20*b* are smaller than the recesses 20*c*.

The housing in this embodiment is intended to be disposable and is manufactured from vacuum-formed polyethylene. Before delivery to the operating theatre the container and instruments are sterilised and the housing is then preferably covered with a spun bonded olefin lid (not shown), such as that commercially available from DuPont under the trade name tyvek. The lid covers and retains the instruments within the container. To maintain sterilisation of the container and instruments within it the container is double bagged for supply to the operating theatre. Use of a double bag allows the sterilisation to be maintained, even if the container is stored in a non-sterile environment.

As can readily be seen from FIGS. 1 and 2, each of the containers 2, 4, 6 has the same external dimensions. This simplifies storage of the containers.

In an alternative embodiment the container may be designed to be reusable. In that embodiment the container is preferably manufactured from a robust, decontamination resistant material such as steel or aluminum. The material preferably has the physical properties of robustness, rigidity and the ability to dry quickly. Injection moulded or vacuum formed plastic having these properties may also be used in a reusable embodiment.

In further alternative embodiments the container may simply be appropriately sized and shaped holes in a sheet of cardboard which is then double bagged. In a less preferred embodiment the container may simply be a double bag holding the instruments loose within it. However, all these embodiments share the feature of a system of containers containing size specific instruments of a single size in each container.

In use, the containers of the above described embodiments form part of a larger system of containers that together contain all the instruments required for a surgeon to carry out knee replacement surgery. This system contains a number of containers arranged according to the general stages in the surgical procedure, so that in use a pack provides those instruments most likely to be required at a particular point in the surgery.

The larger system includes a number of packs containing size specific instrumentation. These include the system of containers of the embodiment of FIGS. 1 and 2, which relate to femoral finishing and trial instrumentation for the knee replacement. In addition, size specific packs of tibial preparation instrumentation and tibial trial instrumentation are provided.

In addition to the size specific packs, the larger system includes a number of packs that contain size independent instruments. These packs include primary cuts instrumentation, core instrumentation, patella instrumentation and resection gap trialling/ligament tensing instrumentation.

Figure 3:
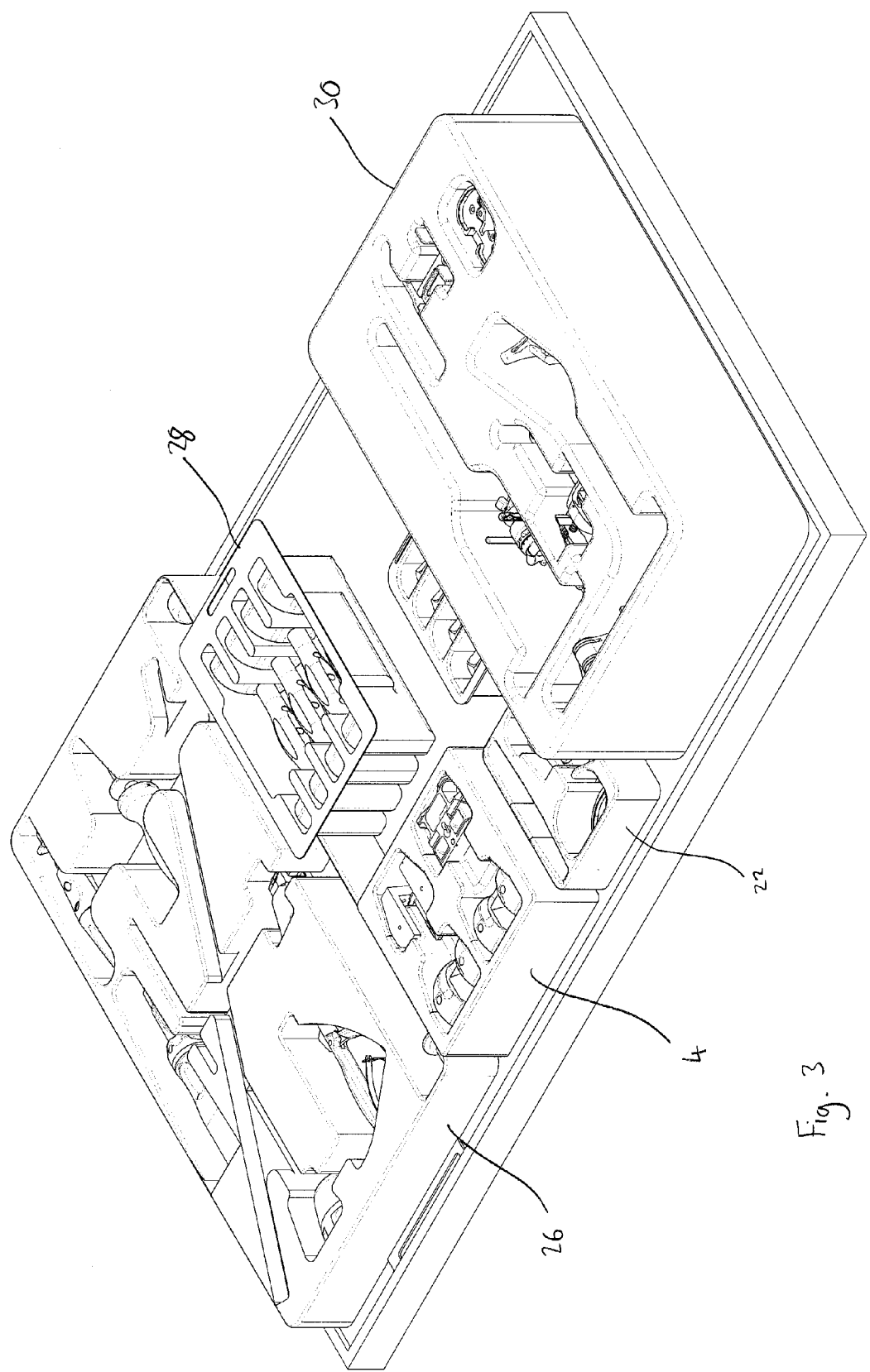
FIG. 3 depicts a perspective view of system of containers as may be used in an operating theatre for knee surgery.
Figure 4:
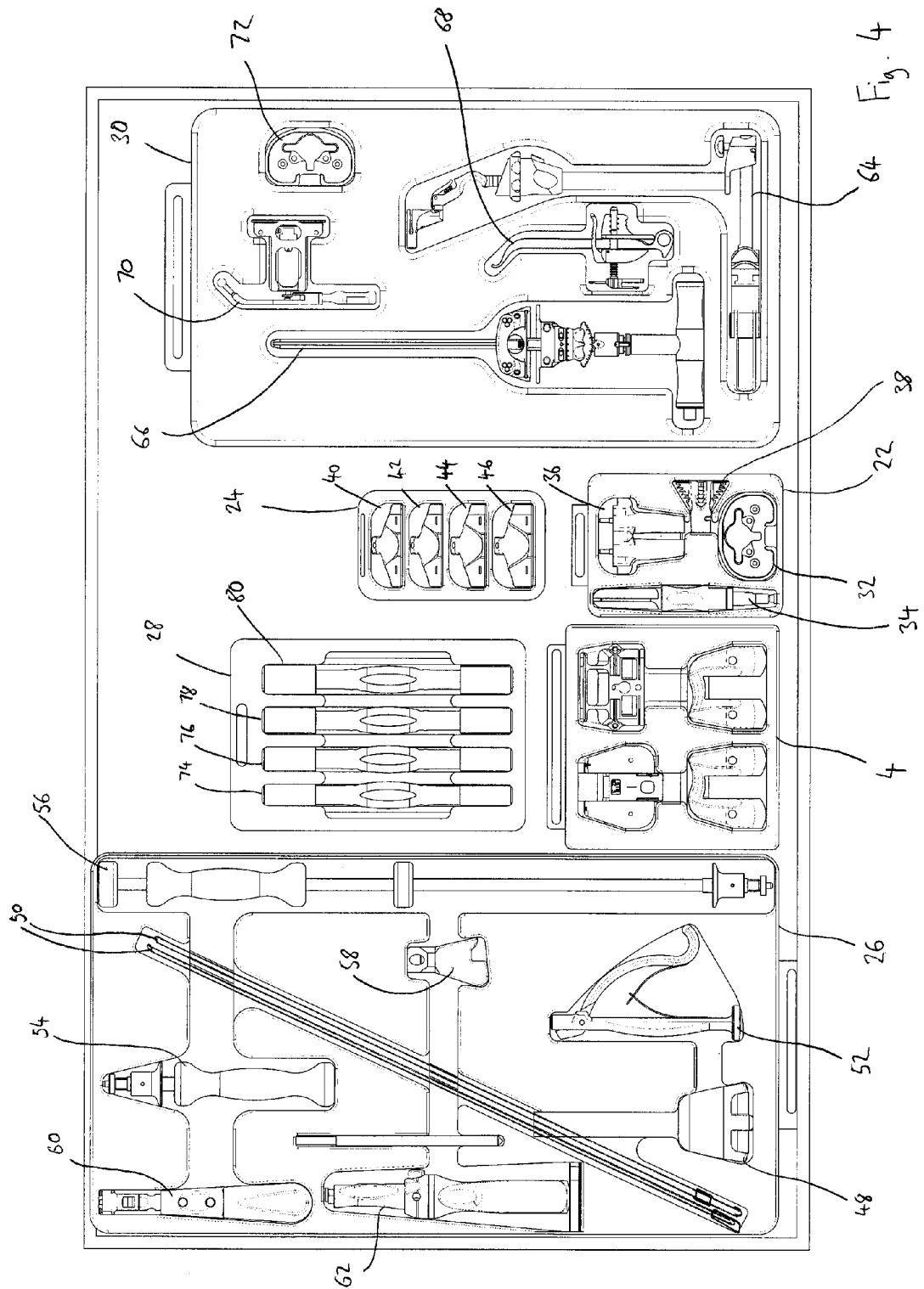
FIG. 4 depicts a plan view of the system of FIG. 3.

FIG. 3 depicts a perspective view of a system of containers such as might be taken into the operating room for knee surgery. FIG. 4 depicts a plan view of FIG. 3 allowing the instruments to be seen more clearly. The containers depicted in FIGS. 3 and 4 are selected from a larger system.

Before carrying out the surgery, the surgeon may have determined the correct size of implant using X-Ray templates. In the example of FIGS. 3 and 4, the surgeon has determined that the correct size of femoral implants is a size 3 implant so a femoral finishing and trialling container 4 is provided containing the size 3 femoral instrumentation.

As can be seen in FIGS. 3 and 4, the other containers are: a size specific tibial preparation instrumentation container 22, a size specific tibial trial container 24, a core instrumentation container 26, a spacer block container 28 and a primary cuts container 30.

The size specific tibial preparation container 22 contains instruments used to prepare the tibia: a tibial template 32, a tibial stem drill 34, a tibial drill/punch guide 36 and a Tibial Punch 38. In alternative embodiments, this container may also contain evaluation bullets; and a tibial handle. (In this embodiment the tibial handle is provided in the core instrumentation container 26). As with the size specific container for femoral finishing and trialling, the size of all these instruments is the same across all the instruments in the container. The P.F.C. sigma system uses the same tibial preparation instrumentation for sizes 1-3 and 4-6, so there are two size specific tibial preparation containers 22 and the appropriate one is selected.

The size specific tibial trial container 24 contains tibial trial implants of a single size but with various thicknesses. It contains a 10 mm thick tibial insert trial 40, a 12.5 mm thick tibial insert trial 42, a 15 mm thick tibial insert trial 44 and a 17.5 mm thick tibial insert trial 46. As with the size specific containers for femoral finishing and trialling, the size is the same across all the instruments in the container.

The core instrumentation container 26 contains core instruments used at various points or more than once in the procedure: a femoral notch impactor 48; alignment rods 50; a pin puller 52; a universal handle 54; a slap hammer 56; a tibial impactor 58, tibial tray handle 60 and a tibial punch handle 62. The core instrumentation container 26 is not size specific.

The primary cut container 30 contains instruments used for proximal tibial resection, distal femoral resection, femoral rotation and femoral and tibial sizing. It contains a proximal tibial resection jig 64; a distal femoral resection jig 66; a tibial stylus 68; a femoral sizing and rotation device 70 and a tibial sizing device 72. This is not a size specific container.

The femoral sizing and rotation device 70 and the tibial sizing device 72 can be used to ensure that the size determined through X-Ray templating is correct. Alternatively, in an embodiment where X Ray templating is not used, the femoral sizing and rotation device 70 and the tibial sizing device 72 can be used to determine the correct size of implant and allowing selection of appropriate size specific containers.

The spacer block pack 28 contains a 10 mm thick spacer block 74, a 12.5 mm thick spacer block 76, a 15 mm thick spacer block 78 and a 17.5 mm thick spacer block 80. This is used for trialling the gap between bone resections. It is not size specific.

Not shown in FIGS. 3 and 4 is a Patella instrumentation container. This includes a patella cutting guide, a patella calliper, a patella drill, a patella cementing clamp, patella trials and a patella drill guide which is not size specific.

During surgery the surgeon can minimise the unused instruments required to be disposed of or decontaminated by using the size specific containers for tibial preparation, tibial insert trials and femoral finishing and trialling. The surgeon may have determined the correct size with x-ray templates and/or will have confirmed the patient's size with the femoral sizing and rotation device 70 and the tibial sizing device 72 in the primary cut container 30. The remaining containers of size specific instruments can be left unused and there is no need to either sterilise them before they can be used in another procedure or to dispose of them without use.

This allows the number of instruments required to be decontaminated or disposed to be minimised compared to the previous system in which a single container contained size specific instruments of many different sizes.

For example, size specific instrumentation might be typically be provided in sizes of 2, 2.5, 3, 4 and 5 for the P.F.C. sigma system. If only a single size of instrument is used, one of the size specific tibial preparation instrumentation container, four of the size specific tibial trial container and four of the femoral finishing and trialling container will be unopened and can be reused without requiring decontamination. Needless decontamination or disposal of thirty-six instruments which have not been used can be avoided. Of course, it will be understood that when more sizes are provided even more instruments can avoid needless decontamination or disposal.

The number of containers required for the all the instrumentation remains manageable so that the identification of the correct instrument can be made easily in the operating room. It also has the benefit of avoiding complicated stock control. For example, if all the instruments were individually packaged, the stock control required in the hospital would be more complicated than the present invention.

In this embodiment the instruments are sterilised within the containers and packaging and delivered ready for use in the operating room.

In an alternative embodiment, the instruments may be processed through a hospital decontamination process of washing followed by sterilisation and delivery to the theatre. In this embodiment, the container is designed to allow the instruments to be washed and sterilised while in place in the container.

It will be appreciated that the present invention can easily be adapted depending on the number of different sizes used in a particular surgical procedure.

In an alternative embodiment the size specific instrumentation may be provided together with the measuring instruments for the trial implants. However, it is presently preferred to include the measuring instruments in a non-size specific container to avoid duplication of instruments.

In another alternative embodiment the size specific containers may be split further, for example into separate containers for the left femoral trial and the right femoral trial. However, this is presently less preferred as it increases the packaging costs and the complexity of the system.

Although the embodiments described above relate to a knee replacement system, it will be appreciated that the present invention can be applied to any other surgical procedure, and in particular other orthopaedic surgical procedures, in which size specific instrumentation is used.

The invention claimed is:

1. A system comprising at least:
   a first container containing at least a first surgical instrument of a first type that is size specific and a second surgical instrument of a second type that is size specific, wherein both the first and second instruments are of a first size;
   a second container containing at least a third surgical instrument of the first type and a fourth surgical instrument of the second type, wherein both the third and fourth instruments are of a second size which is different from the first size; and
   a third container containing at least a fifth surgical instrument of a third type which is size independent;
   wherein:
   the first, second, third, fourth and fifth surgical instruments are sterilized within their respective containers;
   the first container contains no instruments of the second size;
   the second container contains no instruments of the first size;
   the third container contains no instruments that are size specific; and
   each container contains only surgical instruments.

2. A system according to claim 1, wherein the fifth surgical instrument is for determining the required size of the first surgical instrument and/or the second surgical instrument.

3. A system according to claim 1 for use in knee surgery, wherein the first and third instruments are a trial femoral implant and the second and fourth instruments are for performing femoral finishing resections suitable for the first or third trial femoral implant, respectively.

4. A system according to claim 3, wherein the first and second containers each contain:
   a notch guide;
   a femoral finishing cutting block;
   a left trial femoral implant; and
   a right trial femoral implant.

5. A system according to claim 1 for use in knee surgery, wherein the first surgical instrument is a tibial trial instrument of a first thickness and a first size, the second surgical instrument is a tibial trial instrument of a second thickness and the first size, the third surgical instrument is a tibial trial instrument of the first thickness and a second size, and the fourth surgical instrument is a tibial trial instrument of the second thickness and the second size.

6. A system according to claim 1 for use in knee surgery, wherein the first and second containers contain instruments for femoral finishing and trial and the third container contains at least one of primary cuts instrumentation, core instrumentation, patella instrumentation, resection gap trialling and ligament tensing instrumentation.

7. A system according to claim 6, further comprising fourth and fifth containers containing instruments for tibial preparation and tibial trial.

8. A system according to claim 1, wherein the containers are double bagged and the surgical instruments are sterilised within the containers.

9. A system according to claim 1, wherein the containers are disposable.

10. A system according to claim 1, wherein the containers are reusable.

11. A system according to claim 1, wherein the first and second containers each comprise a housing defining locations for the at least first and second surgical instruments and the at least third and fourth surgical instruments, respectively.

* * * * *